Feb. 3, 1959 L. R. FRAZIER ET AL Plant Pat. 1,805
APPLE TREE
Filed Nov. 20, 1957
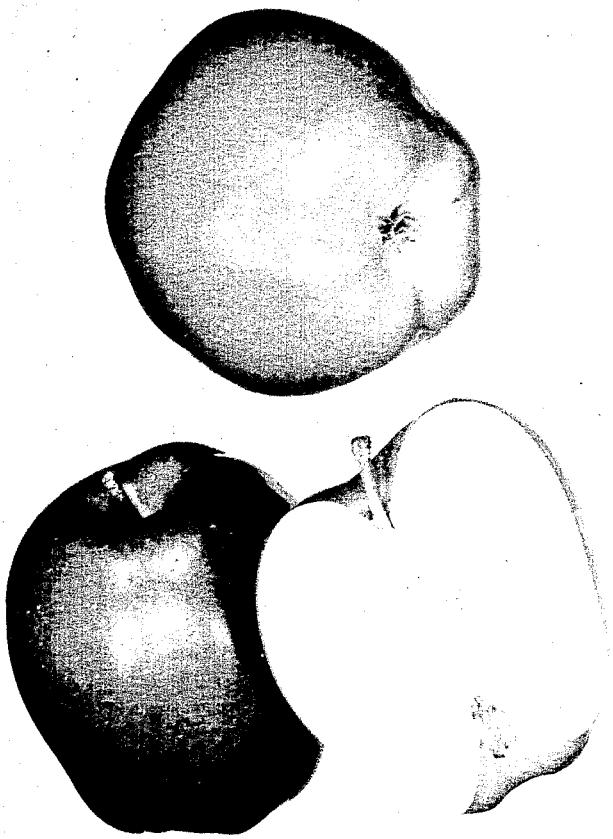
INVENTORS
L. R. Frazier
P. J. Jenkins
BY Robb & Robb
ATTORNEYS United States Patent Office Plant Pat. 1,805
Patented Feb. 3, 1959

1,805

APPLE TREE

Loran R. Frazier and Philip J. Jenkins, Parker, Wash., assignors to Elon J. Gilbert, Yakima, Wash.

Application November 20, 1957, Serial No. 697,759

1 Claim. (Cl. 47—62)

The present invention relates to a new and distinct variety of apple tree which was discovered by us as a whole tree sport during the course of our cultivation and management of an orchard near Parker, Yakima County, Washington, owned by our employer, who is the assignee of this application.

At the time of our initial discovery of the new variety aforesaid, it was observed that one tree amongst an orchard of trees of the variety known as "Starking Delicious" (unpatented) bore fruit of a bright over-all red blush color, without stripes or markings which are typical of the normal fruit of the "Starking Delicious" variety. Closer inspection and subsequent continuous observation and tests for several years showed that this new color characteristic of the sport was fixed and established, and in addition, it was found that the new sport consistently developed its characteristic over-all coloring considerably earlier than the fruit of "Starking Delicious" by at least ten days. Accordingly, the new variety is definitely distinguished from "Starking Delicious" and other strains of that variety, as well as from all other varieties of which we are aware, and the more attractive appearance and early coloring habit of the fruit of the new variety enhance its value for commercial fruit production.

The new sport has been asexually reproduced by grafting, as performed near Yakima, Washington.

In comparison with the variety "Royalred Delicious" (Plant Patent No. 1,278), which is one of the blush-type strains of "Starking Delicious," the fruit of our new variety colors much earlier (usually from 5 to 10 days earlier) and has a heavier color factor, with the color more evenly spaced all over, but the color is not nearly as dark as that of the "Chelan Red" variety (unpatented). The deep Oxblood Red color of the latter variety tends to give the appearance and impression of fruit which has lost most of its life and freshness even when still firm, while the over-all lighter and brighter coloring of the fruit of our new variety is far more attractive to the eye and more conducive to a fresh and zestful appearance.

The accompanying drawing shows typical specimens of the fruit of our new variety, with one of the specimens shown in cross-section, as depicted in color as nearly true as it is reasonably possible to make the same in a color illustration of this character.

The following is a detailed description of the new variety, with color terminology in accordance with Ridgway's Color Standards and Nomenclature, except where general color terms of ordinary dictionary significance are obvious, as based upon observations made from specimens grown near Yakima, Washington:

Tree: Medium size; vigorous; spreading; tall; open; rapid-growing; hardy; productive; regular bearer.

*Trunk.*—Medium stockiness; smooth.

*Branches.*—Medium thickness; smooth; branching. Color—brown. Lenticels—numerous; medium size.

*Leaves.*—Medium size; medium length (about 4 inches); medium width (about 2 inches); medium thickness; taper-pointed; rugose. Color—medium green. Margin—crenate; finely serrate. Petiole—medium length (about 2 inches); medium thickness.

Flowers: Medium early (first bloom about April 17–23 and full bloom about May 3–9); medium size. Color—white, with pink tinge.

Fruit: Maturity when described—between September 15 and September 25.

*Size.*—Uniform. Axial diameter—about 3½ inches. Transverse diameter—about 3⅓ inches.

*Form.*—Uniform; symmetrical; regular; globose; with 5-pointed calyx end.

*Seed cavity.*—Symmetrical; acuminate. Depth—about ½ inch. Breadth—about ¾ inch.

*Basin.*—Symmetrical; flaring; narrow.

*Stem.*—Clubbed; medium stoutness; about 1 inch long; bracts wanting.

*Calyx.*—Closed; segments persistent; lanceolate. Length—about ¼ inch; imbricate at base; ascending. Outer surface—pubescent. Inner surface—pubescent.

*Eye.*—Small; partially closed.

*Skin.*—Thin; smooth; glossy; waxed. Dots—many, small; color — white; distribution — random. Ground color—red. Color markings—absent.

*Bloom.*—Moderate.

*Distribution.*—Good

*General color effect.*—About midway between Carmine, Plate 1, and Oxblood Red, Plate 1 (Ridgway).

*Flesh.*—Juicy. Color—white, with greenish tint. Texture—firm; fine; crisp. Flavor—mild; rich. Aroma—distinct. Quality—best.

*Core.*—Sessile. Bundle area—small; orbicular; symmetrical. Halves of core—equal. Bundles—inconspicuous; color—green. Core lines—clasping; indistinct in cross-section. Carpellary area—indistinct; small. Calyx tube—glabrous toward base; urn-shaped; short funnel stem; depth to shoulder about ¼ inch; entire depth about ¼ inch.

*Styles.*—Fleshy at base; united.

*Axillary cavity.*—Wanting.

*Seed cells.*—Axile; closed. Cell walls—tough; about ½ inch long; about 3/16 inch broad. Longitudinal section — orbicular; acute. Surface — smooth. Cross section—narrow.

Seeds:

*Number.*—8 perfect; 2 per cell. Length—about ¼ inch. Breadth—about 3/32 inch.

*Form.*—Acuminate.

*Color.*—Brown.

Insect and disease resistance: Good resistance to mites, spiders, and other common insects, and to mildew and blight, as determined by comparison with other varieties grown under comparable cultural conditions near Yakima, Washington.

Use: Market; dessert.

Keeping quality: Good; about 100 days in ordinary storage.

We claim:

A new and distinct variety of apple tree, substantially as herein shown and described, characterized particularly as to novelty by the bright, over-all red blush of its fruit and freedom from stripes and other markings, and by the early coloring habit of its fruit which averages at least ten days earlier than the coloring of fruit of the variety "Starking Delicious" (unpatented).

References Cited in the file of this patent

Publications:

1954 Proceedings of The Washington State Horticultural Association, page 273.

Proceedings of The Washington State Horticultural Association, December 1955, page 231.

The Goodfruit Grower, Yakima, Washington, November 27, 1957.